(12) United States Patent
Ji et al.

(10) Patent No.: US 8,828,414 B2
(45) Date of Patent: Sep. 9, 2014

(54) BIOCIDAL COMPOSITION OF 2,6-DIMETHYL-M-DIOXANE-4-OL ACETATE AND METHODS OF USE

(75) Inventors: Kathy J. Ji, Shanghai (CN); Donald J. Love, Midland, MI (US); Jon B. Raymond, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/203,875

(22) PCT Filed: Mar. 26, 2009

(86) PCT No.: PCT/CN2009/071023
§ 371 (c)(1),
(2), (4) Date: Aug. 30, 2011

(87) PCT Pub. No.: WO2010/108323
PCT Pub. Date: Sep. 30, 2010

(65) Prior Publication Data
US 2012/0009176 A1   Jan. 12, 2012

(51) Int. Cl.
| | |
|---|---|
| *A01N 25/02* | (2006.01) |
| *A01N 31/02* | (2006.01) |
| *A01N 33/00* | (2006.01) |
| *A01N 33/14* | (2006.01) |
| *A01N 43/32* | (2006.01) |
| *A01N 35/02* | (2006.01) |

(52) U.S. Cl.
CPC ............. *A01N 35/02* (2013.01); *A01N 43/32* (2013.01)
USPC ........ 424/405; 424/78.09; 514/452; 514/579; 514/718; 514/727

(58) Field of Classification Search
None
See application file for complete search history.

(56) References Cited

U.S. PATENT DOCUMENTS 3,469,002 A    9/1969  Moyer, Jr. et al.
2010/0078393 A1*  4/2010  Yin ............................. 210/764

FOREIGN PATENT DOCUMENTS

| GB | 2393907 A | 4/2004 |
|---|---|---|
| GB | 2393911 A | 4/2004 |
| WO | 2009/015088 A2 | 1/2009 |
| WO | 2010/108324 A1 | 9/2010 |

* cited by examiner

*Primary Examiner* — Neil Levy
(74) *Attorney, Agent, or Firm* — Tifani M. Edwards

(57) ABSTRACT

Provided are biocidal compositions comprising 2,6-dimethyl-m-dioxane-4-ol acetate and a non-formaldehyde releasing biocidal compound selected from the group consisting of: a brominated nitroalkanol, a 2-halo-2-(halomethyl) glutaronitrile, and 2-phenoxyethanol. The compositions are useful for controlling microorganisms in aqueous or water containing systems.

7 Claims, No Drawings

BIOCIDAL COMPOSITION OF 2,6-DIMETHYL-M-DIOXANE-4-OL ACETATE AND METHODS OF USE

This is a §371 application of PCT International Patent Application Number PCT/CN2009/071023 filed Mar. 26, 2009, which is incorporated herein by reference in its entirety.

FIELD OF THE INVENTION

The invention relates to biocidal compositions and methods of their use for the control of microorganisms in aqueous and water containing systems. The compositions comprise 2,6-dimethyl-m-dioxane-4-ol together with a second biocide.

BACKGROUND OF THE INVENTION

Aqueous-based materials often need protection from microbial degradation and/or spoilage during shelf life and use. Preservatives are used to control microbial degradation and/or spoilage in aqueous materials, however, sometimes they are incapable of providing effective control over a wide range of microorganisms, even at high use concentrations. In addition, preservatives are often a costly component of a product. While combinations of different biocides are sometimes used to provide overall control of microorganisms in a particular end use environment, there is a need for additional combinations of microbicides having enhanced activity against various strains of microorganisms. There is also a need for combinations that utilize lower levels of individual microbicides for environmental and economic benefits.

BRIEF SUMMARY OF THE INVENTION

In one aspect, the invention provides biocidal (i.e., preservative) compositions. The compositions are useful for controlling microorganisms in aqueous or water containing systems. The compositions of the invention comprise 2,6-dimethyl-m-dioxane-4-ol acetate together with a non-formaldehyde releasing biocidal compound selected from the group consisting of: a brominated nitroalkanol, a 2-halo-2-(halomethyl)glutaronitrile, and 2-phenoxyethanol.

In a second aspect, the invention provides a method for controlling microorganisms in aqueous or water containing systems. The method comprises treating the system with a biocidal composition as described herein.

DETAILED DESCRIPTION OF THE INVENTION

As noted above, the invention provides biocidal compositions and methods of using them in the control of microorganisms. The compositions comprise 2,6-dimethyl-m-dioxane-4-ol acetate ("dimethoxane") together with a non-formaldehyde releasing biocidal compound selected from the group consisting of: a brominated nitroalkanol, a 2-halo-2-(halomethyl)glutaronitrile, and 2-phenoxyethanol. It has surprisingly been discovered that combinations of dimethoxane with non-formaldehyde releasing biocidal compounds described herein, at certain weight ratios, are synergistic when used for microorganism control in aqueous or water containing media. That is, the combined materials result in improved biocidal properties than would otherwise be expected based on their individual performance. The observed synergy permits reduced amounts of the materials to be used to achieve acceptable biocidal properties, thus potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation.

In a first embodiment of the invention, the non-formaldehyde releasing biocidal compound is a brominated nitroalkanol. Preferably, the brominated nitroalkanol compound is of the formula I:

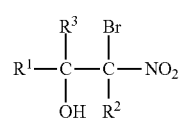

wherein $R^1$ is hydrogen, $C_1$-$C_{12}$ alkyl, or phenyl-$C_1$-$C_{12}$-alkyl-; $R^3$ is hydrogen, or $R^1$ and $R^3$, together with the carbon to which they are attached, form a $C_5$-$C_7$ cycloalkyl ring; and $R^2$ is hydrogen, methyl, ethyl, hydroxymethyl, or bromine.

Preferred nitroalkanols according to formula I include compounds in which $R^1$ is hydrogen or $C_2$-$C_{11}$ alkyl. Further preferred are compounds in which $R^1$ is methyl, ethyl, n-propyl, n-butyl, or n-hexyl. Also preferred are compounds in which $R^1$ and $R^3$, together with the carbon to which they are attached, form a cyclohexyl ring.

Preferred nitroalkanols according to formula I further include compounds in which $R^3$ is H.

Additionally preferred nitroalkanols according to formula I are compounds in which $R^2$ is hydroxymethyl.

Preferred compounds according to formula I include: $C_2H_5CH(OH)CHBrNO_2$; $CH_2(OH)CBrNO_2CH_2OH$; $nC_3H_7CH(OH)CHBrNO_2$; $CH_3CH(OH)CBrNO_2CH_2OH$; $CH_3CH(OH)CHBrNO_2$; $(CH_3)_2CHCH(OH)CBr_2NO_2$; $nC_5H_{11}CH(OH)CHBrNO_2$; $nC_6H_{13}CH(OH)CHBrNO_2$; $CH_3(OH)CNO_2BrCH_3$; 1-(bromonitromethyl)cyclohexanol; $CH_3CH(OH)CBr_2NO_2$; $C_{11}H_{23}CH(OH)CHBrNO_2$; $CH_2(OH)CHBrNO_2$; $nC_4H_9CH(OH)CHBrNO_2$; $C_2H_5CH(OH)CNO_2BrCH_3$; $CH_2(OH)CNO_2BrC_2H_5$; $C_2H_5CH(OH)CBr_2NO_2$. A particularly preferred nitroalkanol of formula I is $CH_2(OH)CBrNO_2CH_2OH$ (2-bromo-2-nitro-1,3-propanediol).

Preferably, the dimethoxane to brominated nitroalkanol weight ratio in the first embodiment of the invention is between about 1000:1 and about 1:1000, more preferably between about 500:1 and about 1:500, even more preferably between about 100:1 and about 1:100. In a particularly preferred embodiment, the dimethoxane to brominated nitroalkanol weight ratio is between about 45:1 and about 1:2.

Brominate nitroalkanols of formula I are commercially available and/or can be readily prepared by those skilled in the art using well known techniques (see e.g., U.S. Pat. No. 3,558,788, which is incorporated herein by reference). Dimethoxane is commercially available.

In a second embodiment of the invention, the non-formaldehyde releasing biocidal compound is a 2-halo-2-(halomethyl)glutaronitrile compound. Preferably, the compound is of the formula II:

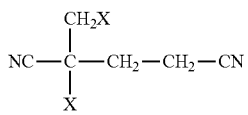

wherein X is bromine or chlorine. A particularly preferred glutaronitrile compound is 2-bromo-2-(bromomethyl)glutaronitrile.

Preferably, the dimethoxane to dihalomethylglutaronitrile weight ratio in the second embodiment of the invention is between about 100:1 and about 1:100, more preferably between about 50:1 and about 1:50, even more preferably between about 50:1 and about 1:1. In further preferred embodiments, the weight ratio is between about 39:1 and about 2:1.

Glutaronitriles of formula II are commercially available and/or can be readily prepared by those skilled in the art using well known techniques (see e.g., U.S. Pat. No. 3,877,922).

In a third embodiment, the non-formaldehyde releasing biocidal compound is phenoxyethanol. Preferably, the dimethoxane to phenoxyethanol weight ratio in the third embodiment of the invention is between about 100:1 and about 1:100, more preferably between about 50:1 and about 1:50, even more preferably between about 1:1 and about 1:30. In further preferred embodiments, the weight ratio is between about 1:6 and about 1:29.

The compositions of the invention are useful at controlling microorganism growth in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oilfield water, pulp and paper water, cooling water), oilfield functional fluids such as drilling muds and fracturing fluids, and fuels. Preferred aqueous systems are detergents, personal care, household and industrial products, and paints/coatings. Particularly preferred are paints and coatings, detergents, and textile fluids such as spin finishes.

A person of ordinary skill in the art can readily determine, without undue experimentation, the concentration of the composition that should be used in any particular application. By way of illustration, a suitable actives concentration (total for both dimethoxane and the second biocide) is typically between 0.001 and 1 weight percent, preferably between 0.01 and 0.1 weight percent, based on the total weight of the aqueous or water containing system including the biocides.

The components of the composition can be added to the aqueous or water containing system separately, or preblended prior to addition. A person of ordinary skill in the art can readily determine the appropriate method of addition. The composition can be used in the system with other additives such as, but not limited to, surfactants, ionic/nonionic polymers and scale, corrosion inhibitors, oxygen scavengers, and/or additional biocides.

The following examples are illustrative of the invention but are not intended to limit its scope.

EXAMPLES

General

Biocides. The following biocides are tested in these examples.

2,6-Dimethyl-m-dioxan-4-ol acetate (dimethoxane or "DMX") is used as BIOBAN™ DXN, 87% active, available from The Dow Chemical Company.

2-Bromo-2-nitropropane-1,3-diol ("BNPD") is used as BIOBAN™ BP-30, 30% active BNPD, available from The Dow Chemical Company.

2-Bromo-2-(bromomethyl)glutaronitrile ("DBGN") is obtained from Alfa Aesar.

2-Phenoxyethanol (2-PE) is used as DOWANOL™ EPh, available from The Dow Chemical Company.

Synergy Calculations. The reported synergy indexes are measured and calculated using the formula described below. In this approach, a synergy index of 1 indicates additivity. If the index is less than 1, synergy has occurred, while a synergy index greater than 1 indicates antagonism.

$$\text{Synergy index} = C_A/C_a + C_B/C_b$$

$C_a$=minimal concentration of antimicrobial A, alone, producing a 4 $\log_{10}$ microbial kill $C_b$=minimal concentration of antimicrobial B, alone, producing a 4 $\log_{10}$ microbial kill $C_A$ and $C_B$=the concentrations of antimicrobials A and B, in combination, producing the required microbial kill (a 4 $\log_{10}$ microbial kill unless indicated otherwise in a particular Example).

Example 1

Evaluation of dimethoxane/2-Bromo-2-nitropropane-1,3-diol In Spinning Finish Emulsion In this Example, the antimicrobial profiles of dimethoxane (DMX), 2-bromo-2-nitropropane-1,3-diol (BNPD) and combinations of DMX and BNPD are evaluated in a spinning finish emulsion. The spinning finish emulsion is determined to be free of microbial contamination prior to initiation of preservative efficacy evaluations. The spinning finish emulsion is prepared by adding 1 part spinning finish oil to 9 parts distilled water followed by 30 minutes of mixing.

Experimental Setup. Tests are conducted in a 96-deep well block format using a total sample volume of 300 to 600 µl for all evaluations. In these samples, no more than 10% of the total volume consists of the biocide and organism solution and all non-matrix additions are normalized for all samples. Each experimental 96-well block contains biocide-treated samples and control samples which lack biocide.

Microorganisms. Twenty-four hour tryptic soy broth cultures are combined in equal parts for formulation inoculation at a final concentration of $5 \times 10^7$ CFU/ml. Organisms are added to each sample of the 96-well block and mixed until homogenous. Additionally, bacterial challenges of the spinning finish emulsion samples occur on days 0, 2, 7, and 14 of the 28-day test period. Organisms utilized: *Pseudomonas aeruginosa* (ATCC#15442), *Pseudomonas aeruginosa* (ATCC#10145), *Enterobacter aerogenes* (ATCC#13048), *Escherichia coli* (ATCC#11229), *Klebsiella pneumoniae* (ATCC#8308), *Staphylococcus aureus* (ATCC#6538), *Salmonella choleraesuis* (ATCC#10708).

Enumeration of Viable Organisms. Sample aliquots are removed, at predetermined time points, for the enumeration of surviving microorganisms. Biocide concentrations resulting in a $\geq 6$ $\log_{10}$ kill of microorganisms, as compared to the preservative-free control, are deemed a significant reduction of viable organisms and are subsequently used for calculating synergy index values. Results are shown in Tables 1.

TABLE 1

DAY 27 synergy calculations (post 4th microbial challenge) for DMX and BNPD in spinning finish emulsion

| Time | DMX:BNPD ratio | DMX alone (ppm) | BNPD alone (ppm) | DMX in combination (ppm) | BNPD in combination (ppm) | Synergy Index |
|---|---|---|---|---|---|---|
| Day 27 | 12:1 | 1339 | 137 | 870 | 75 | 1.19 |
| Day 27 | 9:1 | 1339 | 137 | 669 | 75 | 1.05 |
| Day 27 | 7:1 | 1339 | 137 | 515 | 75 | 0.932 |
| Day 27 | 5:1 | 1339 | 137 | 396 | 75 | 0.843 |
| Day 27 | 4:1 | 1339 | 137 | 305 | 75 | 0.775 |
| Day 27 | 3:1 | 1339 | 137 | 234 | 75 | 0.722 |
| Day 27 | 2:1 | 1339 | 137 | 180 | 75 | 0.681 |

*ppm values represent the active biocide concentration necessary to achieve a $\geq 6$ $\log_{10}$ microbial kill at the specific time point.

Example 2

Evaluation of dimethoxane/2-Bromo-2-nitropropane-1,3-diol in Paint

In this Example, the antimicrobial profiles of dimethoxane (DMX), 2-bromo-2-nitropropane-1,3-diol (BNPD) and combinations of DMX and BNPD are evaluated in a commercial (interior eggshell) water-based latex paint formulation (pH 7.4). The paint formulation is determined to be free of microbial contamination prior to initiation of preservative efficacy evaluations.

Experimental Setup. Tests are conducted in a 96-deep well block format using a total sample volume of 600 μl for all evaluations. In these samples, no more than 10% of the total volume consists of the biocide and organism solution and all non-matrix additions are normalized for all samples. Each experimental 96-well block contains biocide-treated samples and control samples which lack biocide.

Microorganisms. Twenty-four hour tryptic soy broth cultures are combined in equal parts for formulation inoculation at a final concentration of $5 \times 10^6$ CFU/ml. Organisms are added to each sample of the 96-well block and mixed until homogenous. Additionally, bacterial challenges of the paint samples occur on days 0, 2, 7, and 14 of the 28-day test period. Organisms utilized: *Pseudomonas aeruginosa* (ATCC#15442), *Pseudomonas aeruginosa* (ATCC#10145), *Enterobacter aerogenes* (ATCC#13048), *Escherichia coli* (ATCC#11229), *Klebsiella pneumoniae* (ATCC#8308), *Staphylococcus aureus* (ATCC#6538), *Salmonella* choleraesuis (ATCC#10708).

Enumeration of Viable Organisms. Sample aliquots are removed, at predetermined time points, for the enumeration of surviving microorganisms. Numerical values in the data tables listed below represent the $\log_{10}$ viable microorganisms recovered from individual samples at specific time points and biocide concentrations post microorganism addition. Biocide concentrations resulting in a $\geq 4$ $\log_{10}$ kill of microorganisms, as compared to the preservative-free control, are deemed a significant reduction of viable organisms and are subsequently used for calculating synergy index values. The data are shown in Tables 2 and 3.

TABLE 2

DAY 20 viable microorganism enumeration (post 4th microbial challenge) for DMX and BNPD in paint.

| DMX (ppm) | BNPD (ppm) | | | | | | | | DMX alone score | BNPD alone ppm |
|---|---|---|---|---|---|---|---|---|---|---|
| | 450 | 300 | 200 | 133 | 89 | 59 | 40 | 26 | | |
| 1740 | 0 | 0 | 0 | 0 | 0 | 0 | 0 | 0 | 0 | 0 | 450 |
| 1160 | 0 | 0 | 0 | 0 | 0 | 3 | 6 | 4 | 8 | 0 | 300 |
| 773 | 0 | 0 | 0 | 0 | 0 | 8 | 7 | 8 | 8 | 8 | 200 |
| 516 | 0 | 0 | 0 | 8 | 8 | 8 | 8 | 8 | 8 | 8 | 133 |
| 344 | 0 | 0 | 0 | 8 | 8 | 8 | 8 | 8 | 8 | 8 | 89 |
| 229 | 0 | 0 | 0 | 8 | 8 | 8 | 8 | 8 | 8 | 8 | 59 |
| 153 | 0 | 0 | 0 | 7 | 8 | 8 | 8 | 8 | 8 | 8 | 40 |
| 102 | 0 | 0 | 0 | 8 | 8 | 8 | 8 | 8 | 8 | 8 | 26 |
| 0 | 8 | 8 | 8 | 8 | 8 | 8 | 8 | 8 | 8 | 8 | 0 |

TABLE 3

DAY 20 synergy calculations for DMX and BNPD in paint

| Time | DMX:BNPD ratio | DMX alone (ppm) | BNPD alone (ppm) | DMX in combination (ppm) | BNPD in combination (ppm) | Synergy Index |
|---|---|---|---|---|---|---|
| Day 20 | 1:2 | 1740 | 300 | 102 | 200 | .726 |
| Day 20 | 1:1.3 | 1740 | 300 | 153 | 200 | .755 |
| Day 20 | 1:1 | 1740 | 300 | 229 | 200 | .799 |
| Day 20 | 1.7:1 | 1740 | 300 | 344 | 200 | .865 |
| Day 20 | 2.6:1 | 1740 | 300 | 516 | 200 | .964 |
| Day 20 | 6:1 | 1740 | 300 | 773 | 133 | .889 |
| Day 20 | 9:1 | 1740 | 300 | 773 | 89 | .741 |
| Day 20 | 13:1 | 1740 | 300 | 1160 | 89 | .963 |
| Day 20 | 20:1 | 1740 | 300 | 1160 | 59 | .865 |
| Day 20 | 45:1 | 1740 | 300 | 1160 | 26 | .755 |

*Biocide concentrations represented as ppm active DMX or BNPD 1740 ppm active dimethoxane, when used alone, is required to achieve a ≥4 $\log_{10}$ microbial kill following four bacterial challenges. 300 ppm of BNPD when used alone is required to achieve a ≥4 $\log_{10}$ microbial kill under the same testing conditions. Use of various concentration ratios of BNPD and dimethoxane result in a greater $\log_{10}$ reduction in viable microorganisms under the same testing conditions indicating a synergistic combination of biocide actives.

Example 3

Evaluation of Dimethoxane/2-Bromo-2-nitropropane-1,3-diol in Laundry Detergent

A sample of laundry detergent is treated with dimethoxane, BNPD, and combinations thereof. The samples are inoculated with four times over a four-week period with a $5 \times 10^6$ colony forming units per milliliter (CFU/mL) inoculum that includes *Pseudomonas aeruginosa* ATCC#9027, *Enterobacter gergoviae* ATCC#33028 *Pseudomonas putida* ATCC#49128, *Salmonella* choleraesuis ATCC#10708, *Pseudomonas aeruginosa* ATCC#10145, *Pseudomonas aeruginosa* ATCC#15442, *Escherichia coli* ATCC#11229, and *Staphylococcus aureus* ATCC#6538. The samples are inoculated on days 0, 2, 7, and 14 and analyzed for bacteria content on days 0, 1, 2, 3, 6, 8, 13, 15, 20, and 27. The bacteria concentrations are determined by serial dilution (1:10) until a growth endpoint is reached. The sample is scored on a 0-8 scale, based upon the number of serial dilutions required to reach the growth endpoint. For example, if a sample requires four 1:10 dilutions before bacterial growth is lost, then the sample receives a score of 4 which represents between $5 \times 10^4$ and $5 \times 10^5$ viable organisms. Results are shown in Tables 4 and 5.

TABLE 4

DAY 20 viable microorganism enumeration (post 4th microbial challenge) for DMX and BNPD in laundry detergent.

| DMX (ppm) | BNPD (ppm) | | | | | | | | DMX | BNPD score | ppm |
|---|---|---|---|---|---|---|---|---|---|---|---|
| | 750 | 500 | 333 | 222 | 148 | 99 | 66 | 44 | | | |
| 2610 | 0.0 | 0.0 | 0.0 | 0.0 | 0.0 | 0.0 | 0.0 | 0.0 | 0.0 | 0.0 | 750 |
| 1740 | 0.0 | 0.0 | 0.0 | 0.0 | 0.0 | 0.0 | 0.0 | 1.0 | 0.0 | 0.0 | 500 |
| 1160 | 0.0 | 0.0 | 0.0 | 0.0 | 0.0 | 0.0 | 0.0 | 1.0 | 0.0 | 0.0 | 333 |
| 773 | 0.0 | 0.0 | 0.0 | 0.0 | 0.0 | 0.0 | 0.0 | 0.0 | 4.0 | 0.0 | 222 |
| 516 | 0.0 | 0.0 | 0.0 | 0.0 | 0.0 | 0.0 | 0.0 | 0.0 | 6.0 | 0.0 | 148 |
| 344 | 0.0 | 0.0 | 0.0 | 0.0 | 0.0 | 0.0 | 0.0 | 0.0 | 5.0 | 0.0 | 99 |
| 229 | 0.0 | 0.0 | 0.0 | 0.0 | 0.0 | 0.0 | 0.0 | 3.0 | 5.0 | 2.0 | 66 |
| 153 | 0.0 | 0.0 | 0.0 | 0.0 | 0.0 | 0.0 | 0.0 | 4.0 | 5.0 | 4.0 | 44 |
| 0 | 5.0 | 5.0 | 5.0 | 5.0 | 5.0 | 5.0 | 5.0 | 5.0 | 5.0 | 5.0 | 0 |

Several synergistic combinations of dimethoxane and BNPD are found in this study. For example, on day 20, 1160 ppm dimethoxane or 99 ppm BNPD alone are required to achieve a 4 $\log_{10}$ kill of bacteria. 344 ppm dimethoxane/44 ppm BNPD give a synergy ratio of 0.740. Synergistic combinations are shown in Table 5 below.

TABLE 5

DAY 20 synergy calculations for DMX and BNPD in laundry detergent

| Time | DMX:BNPD ratio | DMX alone (ppm) | BNPD alone (ppm) | DMX in combination (ppm) | BNPD in combination (ppm) | Synergy Index |
|---|---|---|---|---|---|---|
| Day 20 | 8:1 | 1160 | 99 | 344 | 44 | 0.740 |

Example 4

Evaluation of Dimethoxane/Dibromoglutaronitrile in Laundry Detergent

A sample of laundry detergent is treated with dimethoxane, dibromoglutaronitrile, and combinations thereof. The samples are inoculated with four times over a four-week period with a $5 \times 10^6$ colony forming units per milliliter (CFU/mL) inoculum that includes *Pseudomonas aeruginosa* ATCC#9027, *Enterobacter gergoviae* ATCC#33028 *Pseudomonas putida* ATCC#49128, *Salmonella* choleraesuis ATCC#10708, *Pseudomonas aeruginosa* ATCC#10145, *Pseudomonas aeruginosa* ATCC#15442, *Escherichia coli* ATCC#11229, and *Staphylococcus aureus* ATCC#6538. The samples are inoculated on days 0, 2, 7, and 14 and analyzed for bacteria content on days 0, 1, 2, 3, 6, 8, 13, 15, 20, and 27. The bacteria concentration is determined by serial dilution (1:10) until a growth endpoint is reached. The sample is scored on a 0-8 scale, based upon the number of serial dilutions required to reach the growth endpoint. For example, if a sample requires four 1:10 dilutions before bacterial growth is lost, then the sample receives a score of 4 which represents between $5 \times 10^4$ and $5 \times 10^5$ viable organisms. A score of 2 or less is considered passing. Tables 6 and 7 below summarize time points at which synergistic combinations of dimethoxane and dibromoglutaronitrile (DBGN) are found.

TABLE 6

Day 20 viable microorganism enumeration for dimethoxane and dibromoglutaronitrile in laundry detergent

| DMX (ppm) | DBGN (ppm) | | | | | | | | DMX Alone | DBGN score | DBGN Alone ppm |
|---|---|---|---|---|---|---|---|---|---|---|---|
| | 50 | 33 | 22 | 15 | 10 | 7 | 4 | 3 | | | |
| 1305 | 0 | 0 | 0 | 0 | 0 | 0 | 0 | 0 | 0 | 0 | 50 |
| 870 | 0 | 0 | 0 | 0 | 0 | 0 | 0 | 0 | 2 | 3 | 33 |
| 580 | 0 | 0 | 0 | 0 | 0 | 1 | 2 | 3 | 2 | 7 | 22 |
| 387 | 0 | 0 | 0 | 0 | 1 | 3 | 3 | 3 | 3 | 8 | 15 |
| 258 | 0 | 0 | 2 | 2 | 2 | 6 | 5 | 8 | 7 | 8 | 10 |
| 172 | 0 | 0 | 1 | 3 | 8 | 8 | 8 | 8 | 8 | 8 | 7 |
| 115 | 0 | 0 | 6 | 6 | 8 | 8 | 8 | 8 | 8 | 8 | 4 |
| 76 | 0 | 0 | 6 | 8 | 8 | 8 | 8 | 8 | 8 | 8 | 3 |
| Controls | 8 | 8 | 8 | 8 | 8 | 8 | 8 | 8 | 8 | 8 | 0 |

TABLE 7

Day 20 synergistic combinations dimethoxane and dibromoglutaronitrile in laundry detergent

| | DMX:DBGN Ratio | DMX (ppm) | DBGN (ppm) | Synergy Index |
|---|---|---|---|---|
| Min alone | | 580 | 50 | |
| Combination 1 | 2:1 | 77 | 33 | 0.79 |
| Combination 2 | 3:1 | 115 | 33 | 0.86 |
| Combination 3 | 5:1 | 172 | 33 | 0.96 |
| Combination 4 | 8:1 | 172 | 22 | 0.74 |
| Combination 5 | 12:1 | 258 | 22 | 0.88 |
| Combination 6 | 17:1 | 258 | 15 | 0.74 |
| Combination 7 | 26:1 | 258 | 10 | 0.64 |
| Combination 8 | 39:1 | 386 | 10 | 0.87 |

Example 5

Evaluation of Dimethoxane and 2-Phenoxyethanol (2-PE) in Laundry Detergent

In this Example, a sample of laundry detergent is treated with dimethoxane, 2-phenoxyethanol (2-PE), and combinations thereof. The same experimental procedure is used as outlined above in Example 4. Tables 8 and 9 below summarize the synergistic combinations found.

TABLE 8

Day 27 viable microorganism enumeration for dimethoxane and 2-phenoxyethanol in laundry detergent

| DMX (ppm) | 2-PE (ppm) | | | | | | | | DMX Alone | 2-PE score | 2-PE ppm |
|---|---|---|---|---|---|---|---|---|---|---|---|
| | 10000 | 6667 | 4444 | 2963 | 1975 | 1317 | 878 | 585 | | | |
| 2610 | 0 | 0 | 0 | 0 | 0 | 0 | 0 | 0 | 0 | 0 | 10000 |
| 1740 | 0 | 0 | 0 | 0 | 0 | 0 | 0 | 0 | 0 | 6 | 6667 |
| 1160 | 0 | 0 | 0 | 0 | 0 | 0 | 0 | 0 | 0 | 6 | 4444 |
| 773 | 0 | 0 | 0 | 0 | 0 | 0 | 0 | 0 | 0 | 5 | 2963 |
| 516 | 0 | 0 | 0 | 0 | 0 | 5 | 5 | 5 | 6 | 7 | 1975 |
| 344 | 0 | 0 | 0 | 0 | 0 | 3 | 4 | 5 | 6 | 7 | 1317 |
| 229 | 0 | 0 | 0 | 1 | 2 | 3 | 4 | 5 | 6 | 7 | 878 |
| 153 | 0 | 0 | 0 | 0 | 1 | 3 | 6 | 4 | 7 | 7 | 585 |
| Controls | 4 | 4 | 4 | 4 | 4 | 4 | 4 | 4 | 4 | 4 | 0 |

TABLE 9

Day 27 synergistic combinations of dimethoxane and 2-phenoxyethanol in laundry detergent

|  | Dimethoxane:2-PE Ratio | Dimethoxane (ppm) | 2-PE (ppm) | Synergy Index |
|---|---|---|---|---|
| Min alone |  | 773 | 10000 |  |
| Combination 1 | 1:13 | 153 | 1975 | 0.40 |
| Combination 2 | 1:19 | 153 | 2963 | 0.49 |
| Combination 3 | 1:6 | 344 | 1975 | 0.64 |
| Combination 4 | 1:29 | 153 | 4444 | 0.64 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A composition comprising:
2,6-dimethyl-m-dioxane-4-ol acetate; and
a non-formaldehyde releasing biocidal compound selected from the group consisting of:
$CH_2(OH)CBrNO_2CH_2OH$ (2-bromo-2-nitro-1,3-propanediol), a 2-halo-2-(halomethyl)glutaronitrile, and 2-phenoxyethanol wherein the 2,6-dimethyl-m-dioxane-4-ol acetate to 2-phenoxyethanol weight ratio is between 45:1 and 1:29, wherein the 2,6-dimethyl-m-dioxane-4-ol acetate to a 2-halo-2-(halomethyl)glutaronitrile weight ratio is between 39:1 and 2:1, and the 2,6-dimethyl-m-dioxane-4-ol acetate to 2-bromo-2-nitro-1,3-propanediol weight ratio is between 45:1 and 1:2.

2. A composition according to claim 1 wherein the 2-halo-2-halomethyl)glutaronitrile compound is of the formula II:

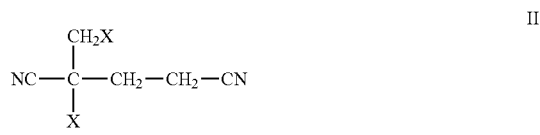

wherein X is bromine or chlorine.

3. A composition according to claim 2 wherein the 2-halo-2-(halomethyl)glutaronitrile compound is 2-bromo-2-(bromomethyl)glutaronitrile.

4. A composition according to claim 1 further comprising one or more surfactants, ionic/nonionic polymers and scale, corrosion inhibitors, oxygen scavengers or additional biocides.

5. A method for controlling microorganisms in an aqueous or water containing system, the method comprising treating the system with a composition according to claim 1.

6. A method according to claim 5 wherein the aqueous or water containing system is selected from paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, spin finishes; metalworking fluids, construction products, personal care products, textile fluids such as spin finishes, industrial process water, oilfield functional fluids such as drilling muds and fracturing fluids, and fuels.

7. A method according to 6 wherein the aqueous or water containing system is selected from personal care, household and industrial products, textile fluids, and paints and coatings.

* * * * *